United States Patent
Herman et al.

(10) Patent No.: US 9,301,961 B2
(45) Date of Patent: Apr. 5, 2016

(54) AUTOIMMUNE AND INFLAMMATORY DISORDER THERAPY

(75) Inventors: Jean Herman, Heverlee (BE); Thierry Louat, Heverlee (BE); Qiuya Huang, Leuven (BE); Bart Vanderhoydonck, Diest (BE); Mark Waer, Heverlee (BE); Piet Herdewijn, Rotselaar (BE)

(73) Assignee: Katholieke Universiteit Leuven, K.U. Leuven R&D, Leuven (BE)

( * ) Notice: Subject to any disclaimer, the term of this patent is extended or adjusted under 35 U.S.C. 154(b) by 99 days.

(21) Appl. No.: 14/343,416

(22) PCT Filed: Sep. 7, 2012

(86) PCT No.: PCT/EP2012/067574
§ 371 (c)(1),
(2), (4) Date: Jun. 23, 2014

(87) PCT Pub. No.: WO2013/034738
PCT Pub. Date: Mar. 14, 2013

(65) Prior Publication Data
US 2014/0294870 A1    Oct. 2, 2014

(30) Foreign Application Priority Data
Sep. 9, 2011   (GB) .................................. 1115665.0

(51) Int. Cl.
*A61K 31/426* (2006.01)
*G01N 33/564* (2006.01)
*A61K 31/5377* (2006.01)
*A61K 31/519* (2006.01)
*G01N 33/573* (2006.01)

(52) U.S. Cl.
CPC ............ *A61K 31/5377* (2013.01); *A61K 31/426* (2013.01); *A61K 31/519* (2013.01); *G01N 33/564* (2013.01); *G01N 33/573* (2013.01); *G01N 2333/91215* (2013.01); *G01N 2500/02* (2013.01)

(58) Field of Classification Search
CPC   A61K 31/5377; A61K 31/426; A61K 33/573
USPC ........................................ 424/184.1; 435/7.4
See application file for complete search history.

(56) References Cited

FOREIGN PATENT DOCUMENTS

| WO | 2008/070137 A2 | 6/2008 |
|---|---|---|
| WO | 2010/044885 A2 | 4/2010 |
| WO | 2010/103130 A2 | 9/2010 |

OTHER PUBLICATIONS

Kapp-Barnea et al., "Neuronal Calcium Sensor-1 and Phosphatidylinositol 4-Kinase Beta Simulate Extracellular Signal-regulated Kinase 1/2 Signaling by Accelerating Recycling through the Endocytic Recycling Compartment", Molecular Biology of the Cell, 2006, 17(9), 4130-4141.
Chu et al., "Differential effects of the phosphatidylinositol 4-kinases, PI4KII alpha and PI4KIII beta, on Akt activation and apoptosis", Cell Death & Disease, 2010, vol. 1, 8 pages.
Balla et al., "Characterization of Type II Phosphatidylinositol 4-Kinase Isoforms Reveals Association of the Enzymes with Endosomal Vesicular Compartments", Journal of Biological Chemistry, 2002, 277(22), 20041-20050.
Szentpetery et al., "Genetic and functional studies of phosphatidylinositol 4-kinase type III alpha", Biochimica and Biophysica Acta, Molecular and Cell Biology of Lipids, 2011, 1811(7), 476-483.

*Primary Examiner* — Raymond Henley, III
(74) *Attorney, Agent, or Firm* — McDonnell Boehnen Hulbert & Berghoff LLP

(57) ABSTRACT

Compounds that bind to phosphatidylinositol-4-kinase IIIβ (PI4KIIIβ) and inhibit the binding of PI4KIIIβ to its substrate and/or inhibit PI4KIIIβ activity may be used in the treatment and/or prevention of an autoimmune or inflammatory disorder, or organ or cell transplant rejection. A new assay for identifying compounds for use in treating and/or preventing those pathological conditions, which comprises measuring the inhibition of PI4KIIIβ activity, is also disclosed.

13 Claims, 5 Drawing Sheets

A

B

A

B

C

D

AUTOIMMUNE AND INFLAMMATORY DISORDER THERAPY

This application is a US national phase of international Application No. PCT/EP2012/06757%1 filed on Sep. 7, 2012, which claims priority to Great Britain Patent Application No. 1115665.0 filed on Sep. 9, 2011.

FIELD OF THE INVENTION

The present invention relates to inhibitors of phosphatidylinositol-4-kinase IIIβ (PI4KIIIβ) and the use of said compounds as biologically active ingredients, more specifically as medicaments for the treatment of immune and autoimmune disorders, organ and cell transplant rejection. The present invention also relates to an assay for identifying a new compound for use in the treatment and/or prevention of autoimmune and inflammatory disorders, and organ and cell transplant rejection, which comprises measuring the inhibition of PI4KIIIβ activity.

BACKGROUND OF THE INVENTION

Currently used immunosuppressive drugs include antiproliferative agents, such as methotrexate (a 2,4-diaminopyrido [3,2-d]pyrimidine derivative), azathioprine, and cyclophosphamide. Since these drugs affect mitosis and cell division, they have severe toxic effects on normal cells with high turnover rate such as bone marrow cells and the gastrointestinal tract lining. Accordingly, marrow depression and liver damage are common side effects of these antiproliferative drugs.

Anti-inflammatory compounds used to induce immunosuppression include adrenocortical steroids such as dexamethasone and prednisolone. The common side effects observed with the use of these compounds are frequent infections, abnormal metabolism, hypertension, and diabetes.

Other immunosuppressive compounds currently used to inhibit lymphocyte activation and subsequent proliferation include cyclosporine, tacrolimus and rapamycin. Cyclosporine and its relatives are among the most commonly used immunosuppressant drugs. Cyclosporine is typically used for preventing or treating organ rejection in kidney, liver, heart, pancreas, bone marrow, and heart-lung transplants, as well as for the treatment of autoimmune and inflammatory diseases such as Crohn's disease, aplastic anemia, multiple sclerosis, myasthenia gravis, uveitis, biliary cirrhosis, etc. However, cyclosporines suffer from a small therapeutic dose window and severe toxic effects including nephrotoxicity, hepatotoxicity, hypertension, hirsutism, cancer, and neurotoxicity.

Additionally, monoclonal antibodies with immunosuppressant properties, such as OKT3, have been used to prevent and/or treat graft rejection. Introduction of such monoclonal antibodies into a patient, as with many biological materials, induces several side effects, such as dyspnea. Within the context of many life-threatening diseases, organ transplantation is considered a standard treatment and, in many cases, the only alternative to death. The immune response to foreign cell surface antigens on the graft, encoded by the major histocompatibility complex (hereinafter referred to as MHC) and present on all cells, generally precludes successful transplantation of tissues and organs unless the transplant tissues come from a compatible donor and the normal immune response is suppressed. Other than identical twins, the best compatibility, and thus long term success of engraftment, is achieved using MHC identical sibling donors or MHC identical unrelated cadaver donors. However, such ideal matches are difficult to achieve. Further, with the increasing need of donor organs an increasing shortage of transplanted organs currently exists. Accordingly, xenotransplantation has emerged as an area of intensive study, but faces many hurdles with regard to rejection within the recipient organism.

The host response to an organ allograft involves a complex series of cellular interactions among T and B lymphocytes as well as macrophages or dendritic cells that recognize and are activated by foreign antigen. Co-stimulatory factors, primarily cytokines, and specific cell-cell interactions, provided by activated accessory cells such as macrophages or dendritic cells, are essential for T-cell proliferation. These macrophages and dendritic cells either directly adhere to T-cells through specific adhesion proteins or secrete cytokines that stimulate T-cells, such as IL-12 and IL-15. Accessory cell-derived co-stimulatory signals stimulate activation of interleukin-2 (IL-2) gene transcription and expression of high affinity IL-2 receptors in T-cells. IL-2 is secreted by T lymphocytes upon antigen stimulation and is required for normal immune responsiveness. IL-2 stimulates lymphoid cells to proliferate and differentiate by binding to IL-2 specific cell surface receptors (IL-2R). IL-2 also initiates helper T-cell activation of cytotoxic T-cells and stimulates secretion of interferon γ, which in turn activates cytodestructive properties of macrophages. Furthermore, IFN-γ and IL-4 are also important activators of MHC class Il expression in the transplanted organ, thereby further expanding the rejection cascade by enhancing the immunogenicity of the grafted organ. The current model of a T-cell mediated response suggests that T-cells are primed in the T-cell zone of secondary lymphoid organs, primarily by dendritic cells. The initial interaction requires cell-to-cell contact between antigen-loaded MHC molecules on antigen-presenting cells (hereinafter referred as APC) and the T-cell receptor/CD3 complex on T-cells. Engagement of the TCR/CD3 complex induces CD154 expression predominantly on CD4 T-cells that in turn activate the APC through CD40 engagement, leading to improved antigen presentation. This is caused partly by up-regulation of CD80 and CD86 expression on the APC, both of which are ligands for the important CD28 co-stimulatory molecule on T-cells.

However, engagement of CD40 also leads to prolonged surface expression of MHC-antigen complexes, expression of ligands for 4-1 BB and OX-40 (potent co-stimulatory molecules expressed on activated T-cells). Furthermore, CD40 engagement leads to secretion of various cytokines and chemokines (e.g. IL-12, IL-15, TNF-α, IL-1, IL-6, and IL-8), all of which have important effects on both APC and T-cell activation and maturation. Similar mechanisms are involved in the development of autoimmune disease, such as type I diabetes. In humans and non-obese diabetic mice, insulin-dependent diabetes mellitus results from a spontaneous T-cell dependent autoimmune destruction of insulin-producing pancreatic beta cells that intensifies with age. The process is preceded by infiltration of the islets with mononuclear cells (insulitis), primarily composed of T lymphocytes. A delicate balance between auto-aggressive T-cells and suppressor-type immune phenomena determines whether expression of autoimmunity is limited to insulitis or not. Therapeutic strategies that target T-cells have been successful in preventing further progress of the autoimmune disease. These include neonatal thymectomy, administration of cyclosporine, and infusion of anti-pan T-cell, anti-CD4, or anti-CD25 (IL-2R) monoclonal antibodies. The aim of all rejection prevention and autoimmunity reversal strategies is to suppress the patient's immune reactivity to the antigenic tissue or agent, with a minimum of morbidity and mortality. Accordingly, a number of drugs are currently being used or investigated for their immunosuppressive properties. As discussed above, the most commonly used immunosuppressant is cyclosporine, which however has numerous side effects.

In view of the relatively few choices for agents effective at immunosuppression with low toxicity profiles and manageable side effects, there exists a need in the art for identification of alternative immunosuppressive agents and for agents acting as complement to calcineurin inhibition. In particular, there is a continuous need in the art for specific and highly therapeutically active compounds, such as, but not limited to, drugs for treating autoimmune and inflammatory disorders, and organ and cell transplant rejection. Specifically, there is a need in the art to provide immunosuppressive compounds to replace existing drugs having significant side effects and to decrease treatment costs.

SUMMARY OF THE INVENTION

The present inventors have found for the first time that compounds which inhibit phosphatidylinositol-4-kinase IIIβ (PI4KIIIβ) activity exert immunosuppressive effects. These compounds can be used in the treatment of conditions associated with autoimmune and/or inflammatory disorders, and organ and cell transplant rejection. The present inventors have also developed assays that can identify compounds that are capable of inhibiting PI4KIIIβ activity in this manner, and so can be used to identify compounds that may be used in the treatment of autoimmune or inflammatory disorders, or organ or cell transplant rejection.

Accordingly, the invention provides a compound that inhibits phosphatidylinositol-4-kinase IIIβ (PI4KIIIβ) activity for use in the treatment and/or prevention of an autoimmune or inflammatory disorder, or organ or cell transplant rejection.

The invention further provides a method for the treatment and/or prevention of an autoimmune or inflammatory disorder or organ or cell transplant rejection that comprises administering to a patient in need of such treatment an effective amount of a compound that inhibits PI4KIIIβ activity.

The invention also provides an assay for identifying a compound for use in the treatment and/or prevention of an autoimmune or inflammatory disorder or organ or cell transplant rejection comprising measuring:

(a) the binding of PI4KIIIβ to a substrate in a sample comprising PI4KIIIβ, the substrate and the compound; and/or
(b) the activity of PI4KIIIβ in a sample comprising PI4KIIIβ and the compound;

and comparing the binding of PI4KIIIβ to the substrate in (a) or the activity of PI4KIIIβ in (b) to corresponding values from control samples and selecting a compound that inhibits PI4KIIIβ, whereby the selected compound will be useful in the treatment and/or prevention of an autoimmune or inflammatory disorder, or organ or cell transplant rejection.

DETAILED DESCRIPTION OF THE INVENTION

Figure 1:
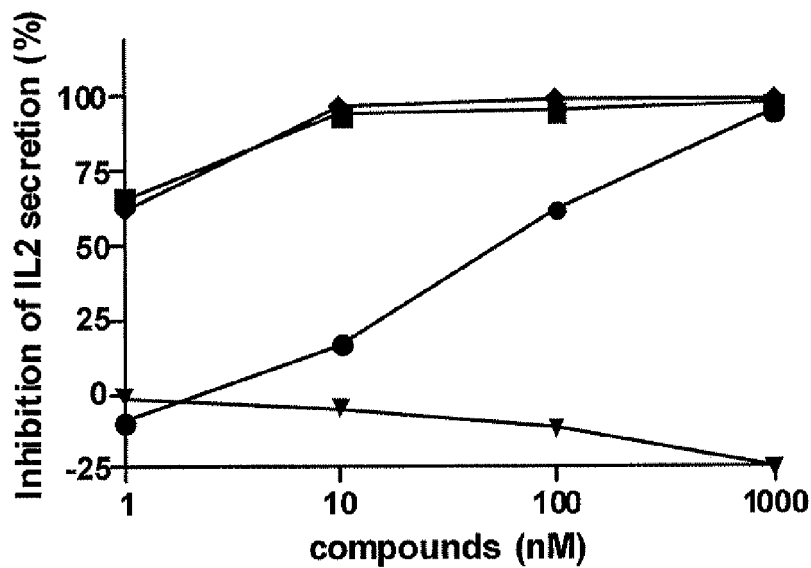
FIG. 1 shows graphs of the inhibition of IL2 secretion (A) and IFNγ secretion (B) by murine splenocytes stimulated with α-CD3 antibodies with increasing concentrations of test compounds.
Figure 1:
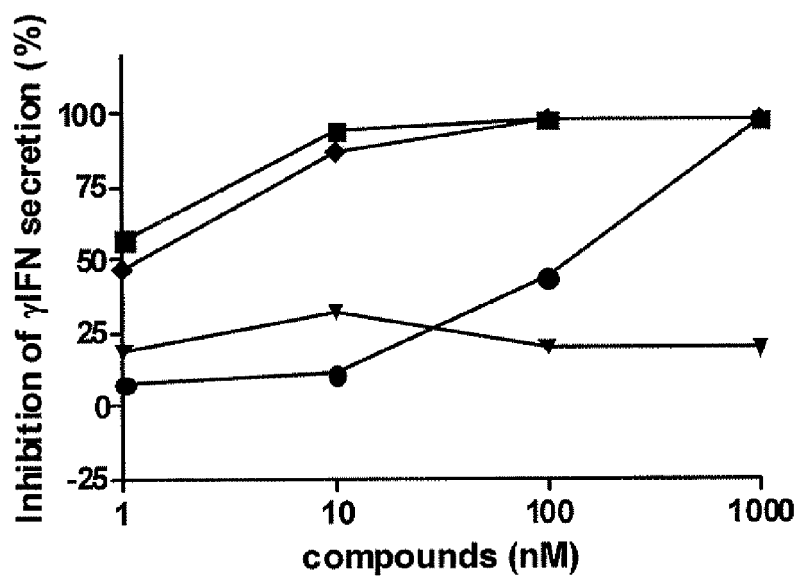

Assays for Identifying Compounds that Inhibit Phosphatidylinositol-4-Kinase (PI4KIIIβ) Activity The present inventors have developed assays for identifying compounds for use in the treatment and/or prevention of an autoimmune or inflammatory disorder or organ or cell transplant rejection by inhibiting phosphatidylinositol-4-kinase IIIβ (PI4KIIIβ) activity. Accordingly, the invention provides assays that are useful for identifying compounds for use in the treatment and/or prevention of an autoimmune or inflammatory disorder or organ or cell transplant rejection by inhibiting PI4KIIIβ activity.

In particular, the assays described herein may be used to identify compounds for use in the treatment and/or prevention of an autoimmune or inflammatory disorder or organ or cell transplant rejection by inhibiting the binding of PI4KIIIβ to its substrate and/or inhibiting the kinase activity of PI4KIIIβ.

In a preferred embodiment, the compounds of use in the invention inhibit the binding of PI4KIIIβ to its substrate and inhibit the kinase activity of PI4KIIIβ.

Assays of the invention may comprise determining whether a test compound inhibits the binding of PI4KIIIβ to its substrate, and hence identify PI4KIIIβ inhibitors. Assays of the invention may alternatively or in addition comprise determining whether a test compound inhibits the kinase activity of PI4KIIIβ.

Assays for identifying compounds of use in the invention may comprise incubating a sample of PI4KIIIβ with a test compound and measuring the extent to which a test compound inhibits the binding of PI4KIIIβ to its substrate. Alternatively, assays for identifying compounds of use in the invention may involve incubating a sample of PI4KIIIβ with a test compound, and measuring the kinase activity of PI4KIIIβ in the presence of the test compound.

The PI4KIIIβ may be purified or present in mixtures, such as in cultured cells, tissue samples, body fluids or culture medium. Assays may be developed that are qualitative or quantitative, with the latter being useful for determining the binding parameters (affinity constants and kinetics) of the test compound to PI4KIIIβ, the binding parameters of the PI4KIIIβ to its substrate in the presence of the test compound, or the kinase activity of PI4KIIIβ in the presence of the test compound.

The amount of PI4KIIIβ bound to its substrate or to the test compound may be determined by measuring the mass of PI4KIIIβ, the molar amount of PI4KIIIβ, the concentration of PI4KIIIβ, and the molarity of PI4KIIIβ. This amount may be given in any appropriate units. For example, the concentration of PI4KIIIβ bound to its substrate or to the test compound may be given in pg/ml, ng/ml or μg/ml. The mass of PI4KIIIβ bound to its substrate or to the test compound may be given in pg, ng or μg.

The amount of PI4KIIIβ bound to its substrate in a sample of interest may be compared with the level of PI4KIIIβ bound to its substrate in another sample, such as a control sample, as described herein. In such a method, the actual amount of PI4KIIIβ bound to its substrate, such as the mass, molar amount, concentration or molarity of PI4KIIIβ bound to its substrate in the samples, may be assessed. The amount of PI4KIIIβ bound to its substrate may be compared with that in another sample without quantifying the mass, molar amount, concentration or molarity of PI4KIIIβ bound to its substrate. Thus, the amount of PI4KIIIβ bound to its substrate in a sample according to the invention may be assessed as a relative amount, such as a relative mass, relative molar amount, relative concentration or relative molarity of PI4KIIIβ bound to its substrate, based on a comparison between two or more samples.

The present inventors have developed methods for identifying compounds of use in the invention comprising determining the effect of test compounds on the binding of PI4KIIIβ to its substrate and/or determining the effect of test compounds on the kinase activity of PI4KIIIβ, and hence identifying inhibitors of PI4KIIIβ activity, whereby the inhibitors thereby identified will be useful in the treatment or prevention of an autoimmune or inflammatory disorder, or organ or cell transplant rejection.

Accordingly, the invention provides an assay for identifying a compound of use in the invention comprising measuring:
  (a) the binding of PI4KIIIβ to a substrate in a sample comprising PI4KIIIβ, the substrate and the compound; and/or
  (b) the activity of PI4KIIIβ in a sample comprising PI4KIIIβ and the compound;
and comparing the binding of PI4KIIIβ to the substrate in (a) or the activity of PI4KIIIβ in (b) to corresponding values from control samples and selecting a compound that inhibits PI4KIIIβ, whereby the selected compound will be useful in the treatment and/or prevention of an autoimmune or inflammatory disorder or organ or cell transplant rejection. The control sample may be identical to the sample being assayed, except that it lacks the test compound and/or it contains a known compound.

The binding affinity of PI4KIIIβ to its substrate may be determined in the presence and absence of the test compound in order to determine whether the test compound decreases the binding affinity of PI4KIIIβ to its substrate.

The test compound may decrease the binding affinity of PI4KIIIβ to its substrate by 2 times, 3 times, 4 times, 5 times, 10 times, 20 times, 30 times, 40 times, 50 times, 60 times, 70 times, 80 times, 90 times, 100 times or more compared to the binding affinity of PI4KIIIβ to its substrate in the absence of the test compound.

The binding affinity may be given in terms of binding affinities ($K_d$) and may be given in any appropriate units, such as μM, nM or pM. The smaller the $K_d$ value, the larger the binding affinity of PI4KIIIβ to its substrate.

The $K_d$ value of PI4KIIIβ for binding to its substrate in the presence of the test compound may be at least 2 times, 3 times, 4 times, 5 times, 10 times, 20 times, 30 times, 40 times, 50 times, 60 times, 70 times, 80 times, 90 times, 100 times greater than the $K_d$ value of PI4KIIIβ for binding to its substrate in the absence of the test compound.

The $K_d$ value of PI4KIIIβ for binding to its substrate in the presence of the test compound may be 100 nM, 1 μM, 10 μM, 50 μM, 100 μM, 200 μM, 300 μM, 400 μM, 500 μM, 600 μM, 700 μM, 800 μM, 900 μM, 1 mM, 10 mM or more. In a preferred embodiment the $K_d$ value of PI4KIIIβ for binding to its substrate in the presence of the test compound is 500 μM or more.

The test compound may decrease the activity of PI4KIIIβ by at least 10%, 20%, 30%, 40%, 50%, 60%, 70%, 80%, 90% or up to 100%, i.e. the test compound may completely abolish the activity of PI4KIIIβ. The activity of PI4KIIIβ is intended to mean any downstream effect of PI4KIIIβ that is initiated when PI4KIIIβ binds to its substrate in the absence of the test compound. In a preferred embodiment, PI4KIIIβ activity means PI4KIIIβ kinase activity. The inhibition of kinase activity may be measured using any appropriate technique.

The ability of a test compound to exert an immunosuppressive effect may be further investigated. Accordingly, the assay of the invention may further comprise measuring the cell proliferation in a population of peripheral blood mononuclear cells (PBMCs) in a sample comprising the PBMC population and the compound, wherein the PBMCs are subjected to an immunogenic stimulus. The cell proliferation in the PBMC population may be measured by any appropriate technique, for example using the mixed lymphocyte reaction (MLR) method. Particular types of PBMC include lymphocytes, and myeloid cells (such as monocytes, macrophages and dendritic cells).

The MLR assay is a fundamental benchmark test for immunosuppressant activity. Most of the conventional immunosuppressive drugs are very potent in the MLR assay, and several of them were discovered by this assay. Therefore, it is appropriate to evaluate the immunosuppressive activity of test compounds with the MLR assay. This screening is used as a predictive in vitro test of in vivo organ transplant rejection. In the MLR assay PBMCs from two individuals are mixed together in tissue culture for several days. Mononuclear cells from incompatible individuals will stimulate each other to proliferate significantly (measured by tritiated thymidine uptake, for example), whereas those from compatible individuals will not. In the one-way MLR test, the mononuclear cells from one of the individuals are inactivated (usually by treatment with mitomycin C or irradiation), thereby allowing only the untreated remaining population of mononuclear cells, such as lymphocytes, to proliferate in response to foreign histocompatibility antigens.

Compounds that Inhibit Phosphatidylinositol-4-Kinase IIIβ (PI4KIIIβ) Activity

The present invention provides compounds that inhibit phosphatidylinositol-4-kinase IIIβ (PI4KIIIβ) activity for use in the treatment and/or prevention of an autoimmune or inflammatory disorder, or organ or cell transplant rejection.

The compounds of use in the invention bind to phosphatidylinositol-4-kinase IIIβ (PI4KIIIβ). Such compounds may bind selectively to PI4KIIIβ. By selective, it will be understood that the compounds bind to the molecule or molecules of interest, in this case PI4KIIIβ, with no significant cross-reactivity to any other molecule, which may include other phosphatidylinositol kinases. Cross-reactivity may be assessed by any suitable method, for example surface plasmon resonance. Cross-reactivity of a compound for PI4KIIIβ with a molecule other than PI4KIIIβ may be considered significant if the compound binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to PI4KIIIβ. A compound that is selective for PI4KIIIβ may bind to another molecule at less than 90%, 85%, 80%, 75%, 70%, 65%, 60%, 55%, 50%, 45%, 40%, 35%, 30%, 25% or 20% the strength that it binds to PI4KIIIβ. Preferably, the compound binds to the other molecule at less than 20%, less than 15%, less than 10%, less than 5%, less than 2% or less than 1% the strength that it binds to PI4KIIIβ.

The $K_d$ value of PI4KIIIβ for binding to its substrate in the presence of the test compound may be at least 2 times, 3 times, 4 times, 5 times, 10 times, 20 times, 30 times, 40 times, 50 times, 60 times, 70 times, 80 times, 90 times, 100 times greater than the $K_d$ value of PI4KIIIβ for binding to its substrate in the absence of the test compound.

The $K_d$ value of PI4KIIIβ for binding to its substrate in the presence of the test compound may be 100 nM, 1 µM, 10 µM, 50 µM, 100 µM, 200 µM, 300 µM, 400 µM, 500 µM, 600 µM, 700 µM, 800 µM, 900 µM, 1 mM, 10 mM or more. In a preferred embodiment the $K_d$ value of PI4KIIIβ for binding to its substrate in the presence of the test compound is 500 µM or more.

The compounds of use in the invention may completely or partially inhibit PI4KIIIβ activity when the compounds bind to PI4KIIIβ. The compound may act to reduce PI4KIIIβ activity by at least 10%, 20%, 30%, 40%, 50%, 60%, 70%, 80%, 90% or 100%. Reduction in PI4KIIIβ activity may be measured by any appropriate technique.

The $K_d$ value of PI4KIIIβ for binding to a test compound of the invention may be 100 µM, 50 µM, 25 µM, 10 µM, 500 nM, 400 nM, 300 nM, 200 nM, 100 nM, 90 nM, 80 nM, 70 nM, 50 nM, 40 nM, 30 nM, 20 nM, 10 nM, 5 nM, 1 nM or less. In a preferred embodiment the $K_d$ value of PI4KIIIβ for binding to the test compound is 50 nM or less.

The compounds of use in the invention may inhibit phosphatidylinositol-4-kinase IIIβ (PI4KIIIβ) activity by decreasing or abolishing the expression of PI4KIIIβ, and so inhibit the amount of PI4KIIIβ present in a patient and so the amount of PI4KIIIβ available for mediating autoimmune or inflammatory disorders, or organ or cell transplant rejection. A compound of use in the invention may inhibit the expression of PI4KIIIβ by 50%, 60%, 70%, 80%, 90% or 100% compared to the level of PI4KIIIβ expression in the absence of the compound. The compounds of use in the invention may inhibit the expression of PI4KIIIβ by any appropriate method, for example via RNAi. The compounds of use in the invention may completely or partially inhibit the immune response to an immunological stimulus. The term "immune response" will be understood to mean any response elicited by the immune system, including $Th_1$, $Th_2$ and $Th_3$ type immune responses. An immunological stimulus means anything that is capable of provoking an immune response, such as an antigen, particularly an auto-antigen.

The test compound may act to reduce the immune response to an immunological stimulus by at least 10%, 20%, 30%, 40%, 50%, 60%, 70%, 80%, 90% or 100%. Reduction in the immune response activity may be measured by any appropriate technique, for example as measured using an MLR assay, reduction in IL2 or IFNγ secretion or other techniques described herein.

The activity of the compounds of use in the invention may be quantified using standard terminology, such as half maximal inhibitory concentration ($IC_{50}$) or half maximal effective concentration ($EC_{50}$) values. $IC_{50}$ values represent the concentration of a compound that is required for 50% inhibition of a specified biological or biochemical function. $EC_{50}$ values represent the concentration of a compound that is required for 50% of its maximal effect. The compounds of use in the invention may have $IC_{50}$ or $EC_{50}$ values of 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 100 µM or less. $IC_{50}$ and $EC_{50}$ values may be measured using any appropriate technique, for example cytokine production can be quantified using ELISA. $IC_{50}$ and $EC_{50}$ values can then be generated using a standard 4-parameter logistic model also known as the sigmoidal dose response model.

Phosphatidylinositol-4-Kinase IIIβ (PI4KIIIβ)

Phosphatidylinositol-4-kinase IIIβ (PI4KIIIβ is a type III phosphatidylinositol kinase that is found in several tissues and is localised primarily to the Golgi apparatus within cells. PI4KIIIβ mediates the phosphorylation of phosphatidylinositol to phosphatidylinositol-4-phosphate.

PI4KIIIβ is the smaller of two forms of the phosphatidylinositol-4-kinase type III (PI4KIII) enzyme, having a molecular weight of approximately 110 kDa. PI4KIIIβ comprises a pleckstrin homology (PH) domain and a catalytic domain. The catalytic domain of PI4KIIIβ shares some degree of similarity with that of the phosphatidylinositol-3-kinases.

PI4KIIIβ has been implicated in the treatment of viral infections (WO 2009/004085). However, the present inventors are the first to teach that compounds that inhibit PI4KIIIβ activity have utility in the treatment of autoimmune or inflammatory disorders, or organ or cell transplant rejection.

Therapeutic Indications

The compounds of use in the present invention are beneficial in the treatment and/or prevention of autoimmune and inflammatory disorders, and organ and cell transplant rejection. Said autoimmune disorder may result from organ or cell transplantation.

The present invention also concerns a pharmaceutical composition comprising a compound of use in the invention and one or more pharmaceutically acceptable excipients. Said pharmaceutical composition may further comprise one or more biologically active drugs being selected from the group consisting of immunosuppressant and/or immunomodulator drugs, and antineoplastic drugs.

The present invention also concerns a method for the treatment and/or prevention of an autoimmune or inflammatory disorder or organ or cell transplant rejection in an animal, comprising the administration of a therapeutically effective amount of a compound of use in the invention, optionally in combination with one or more pharmaceutically acceptable excipients. Said autoimmune disorder may result from organ or cell transplantation.

Said animal may be a mammal. Preferably said mammal is a human being.

Autoimmune disorders to be prevented or treated by the compounds of use in this invention include systemic autoimmune diseases such as, but not limited to, lupus erythematosus, psoriasis, vasculitis, polymyositis, scleroderma, multiple sclerosis, ankylosing spondilytis, rheumatoid arthritis and Sjogren syndrome; auto-immune endocrine disorders such as thyroiditis; and organ-specific autoimmune diseases such as, but not limited to, Addison disease, hemolytic or pernicious anemia, Goodpasture syndrome, Graves disease, idiopathic thrombocytopenic purpura, insulin-dependent diabetes mellitus, juvenile diabetes, uveitis, Crohn's disease, ulcerative colitis, pemphigus, atopic dermatitis, autoimmune hepatitis, primary biliary cirrhosis, autoimmune pneumonitis, autoimmune carditis, myasthenia gravis, glomerulonephritis and spontaneous infertility. Asthma and allergy may also be treated or prevented by compounds of use in this invention.

Transplant rejections to be prevented or treated by the compounds of use in this invention include the rejection of transplanted or grafted organs or cells (both allografts and xenografts), such as but not limited to host versus graft reaction disease. The term "organ" as used herein means all organs or parts of organs in mammals, in particular humans, such as but not limited to kidney, lung, bone marrow, hair, cornea, eye (vitreous), heart, heart valve, liver, pancreas, blood vessel, skin, muscle, bone, intestine or stomach. The term "rejection" as used herein means all reactions of the recipient body or the transplanted organ that 'in the end lead to cell or tissue death in the transplanted organ or adversely affect the functional ability and viability of the transplanted organ or the recipient. In particular, this means acute and chronic rejection reactions. Also included in this invention is preventing or treating the rejection of cell transplants and xenotransplantation. The major hurdle for xenotransplantation is that even before the T lymphocytes, responsible for the rejection of allografts, are activated, the innate immune system, especially T-independent B lymphocytes and macrophages, is activated. This provokes two types of severe and early acute rejection called hyperacute rejection and vascular rejection, respectively. The present invention addresses the problem that conventional immunosuppressant drugs like cyclosporine A are ineffective in xeno-transplantation. The ability of the compounds of this invention to suppress T-independent xeno-antibody production as well as macrophage activation may be evaluated in the ability to prevent xenograft rejection in athymic, T-deficient mice receiving xenogenic hamster-heart grafts.

Pharmaceutical Compositions, Dosages and Dosage Regimes

The present invention provides the use of the compounds of use in the invention as a biologically active ingredient, i.e. active principle, especially as a medicine or for the manufacture of a medicament for treating and/or preventing an autoimmune or inflammatory disorder, or organ or cell transplant rejection. The pathologic conditions and disorders concerned by the said use, and the corresponding methods of prevention or treatment, are detailed hereinabove. Any of the uses mentioned with respect to the present invention may be restricted to a non-medical use (e.g. in a cosmetic composition), a non-therapeutic use, a non-diagnostic use, a non-human use (e.g. in a veterinary composition), or exclusively an in-vitro use, or a use with cells remote from an animal. The invention further relates to a pharmaceutical composition comprising: (a) one or more compounds of use in the invention, and (b) one or more pharmaceutically acceptable carriers.

The compounds of use in the invention may be used in combinations, preferably synergistic combinations, with one or more biologically active drugs being preferably selected from the group consisting of immunosuppressant and/or immunomodulator drugs.

Suitable immunosuppressant drugs for inclusion in the combined compositions or combined preparations comprising a compound of use in this invention belong to a well known therapeutic class. They are preferably selected from the group consisting of cyclosporine A, substituted xanthines (e.g. methylxanthines such as pentoxyfylline), daltroban, sirolimus, tacrolimus, rapamycin (and derivatives thereof such as defined below), leflunomide (or its main active metabolite A771726, or analogs thereof called malononitrilamides), mycophenolic acid and salts thereof (including the sodium salt marketed under the trade name Mofetil®), adrenocortical steroids, azathioprine, brequinar, gusperimus, 6-mercaptopurine, mizoribine, chloroquine, hydroxychloroquine and monoclonal antibodies with immunosuppressive properties (e.g. etanercept, infliximab or kineret). Adrenocortical steroids within the meaning of this invention mainly include glucocorticoids such as but not limited to ciprocinonide, desoxycorticosterone, fludrocortisone, flumoxonide, hydrocortisone, naflocort, procinonide, timobesone, tipredane, dexamethasone, methylprednisolone, methotrexate, prednisone, prednisolone, triamcinolone and pharmaceutically acceptable salts thereof. Rapamycin derivatives as referred herein include O-alkylated derivatives, particularly 9-deoxorapamycins, 26-dihydrorapamycins, 40-O-substituted rapamycins and 28,40-O,O-disubstituted rapamycins (as disclosed in U.S. Pat. No. 5,665,772) such as 40-O-(2-hydroxy)-ethyl rapamycin (also known as SDZ-RAD), pegylated rapamycin (as disclosed in U.S. Pat. No. 5,780,462), ethers of 7-desmethylrapamycin (as disclosed in U.S. Pat. No. 6,440,991) and polyethylene glycol esters of SDZ-RAD (as disclosed in U.S. Pat. No. 6,331,547).

Suitable immunomodulator drugs for inclusion into the combined compositions or combined preparations comprising a compound of use in this invention are preferably selected from the group consisting of acemannan, amiprilose, bucillamine, dimepranol, ditiocarb sodium, imiquimod, inosine pranobex, interferon-$\beta$, interferon-$\gamma$, lentinan, levamisole, lisophylline, pidotimod, romurtide, platonin, procodazole, propagermanium, thymomodulin, thymopentin and ubenimex.

The term "pharmaceutically acceptable carrier or excipient" as used herein in relation to pharmaceutical compositions and combined preparations means any material or substance with which the active principle, i.e. the compound of use in this invention, and optionally the immunosuppressant or immunomodulator may be formulated in order to facilitate its application or dissemination to the locus to be treated, for instance by dissolving, dispersing or diffusing said composition, and/or to facilitate its storage, transport or handling without impairing its effectiveness. The pharmaceutically acceptable carrier may be a solid or a liquid or a gas which has been compressed to form a liquid, i.e. the compositions comprising a compound of use in this invention can suitably be used as concentrates, emulsions, solutions, granulates, dusts, sprays, aerosols, pellets or powders. Suitable pharmaceutical carriers for use in said pharmaceutical compositions and their formulation are well known to those skilled in the art. There is no particular restriction to their selection within the present invention although special attention may need to be paid to the selection of suitable carrier combinations that can assist in properly formulating compounds of use in the invention in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions comprising a compound of use in the present invention may be prepared in any known manner, for instance by homogeneously mixing, dissolving, spray-drying, coating and/or grinding the active ingredients, in a one-step or a multi-step procedure, with the selected carrier material and, where appropriate, the other additives such as surface-active agents. They may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions comprising a compound of use in the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alkanolamine salts of dodecylbenzene sulphonic acid or dibutylnaphthalenesulphonic acid or a naphthalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphosphatidylcholine and their mixtures. Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethylene glycol ether groups and/or 10 to 100 propylene glycol ether groups. Such compounds usually contain from 1 to 5 ethylene glycol units per propylene glycol unit. Representative examples of nonionic surfactants are nonylphenolpolyethoxyethanol, castor oil polyglycolic ethers, polypropylene/polyethylene oxide adducts, tributylphenoxypolyethoxyethanol, polyethylene glycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy $C_{1-4}$alkyl radicals. A more detailed description of surface-active agents suitable for this purpose may be found for instance in "McCutcheon's Detergents and Emulsifiers Annual" (MC Publishing Corp., Ridgewood, N.J., 1981), "Tensid-Taschenbuch", 2nd ed. (Hanser Verlag, Vienna, 1981) and "Encyclopaedia of Surfactants" (Chemical Publishing Co., New York, 1981). Structure-forming, thickening or gel-forming agents may be included into the pharmaceutical compositions and combined preparations comprising a compound of use in the invention. Suitable such agents are in particular highly dispersed silicic acid, such as the product commercially available under the trade name Aerosil; bentonites; tetraalkyl ammonium salts of montmorillonites (e.g. products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations comprising a compound of use in the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations comprising a compound of use in the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzyl alcohol, methyl paraben, propyl paraben and the like; sequestering agents such as ethylenediamine tetraacetic acid; flavouring agents such as natural vanillin; buffers such as citric acid and acetic acid; extenders or bulking agents such as silicates, diatomaceous earth, magnesium oxide or aluminium oxide; densification agents such as magnesium salts; and mixtures thereof. Additional ingredients may be included in order to control the duration of action of the biologically-active ingredient in the compositions and combined preparations comprising a compound of use in the invention. Controlled release compositions may thus be achieved by selecting appropriate polymer carriers such as for example polyesters, polyamino acids, polyvinylpyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems including, but not limited to, liposomes, microspheres, microemulsions, nanoparticles, nanocapsules and so on. Depending on the route of administration, the pharmaceutical composition or combined preparation comprising a compound of use in the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered by way of intracavernosal injection, or may be administered topically, in an ointment, gel or the like, or transdermally, including transscrotally, using a conventional transdermal drug delivery system. Intracavernosal injection can be carried out by use of a syringe or any other suitable device. An example of a hypodermic syringe useful herein is described in U.S. Pat. No. 4,127,118, injection being made on the dorsum of the penis by placement of the needle to the side of each dorsal vein and inserting it deep into the corpora.

When compounds of use in the invention are for use in combination with one or more other biologically active drug, particularly an immunosuppressant or immunomodulator, the compound of use in the invention and the one or more other biologically active drug may be for simultaneous or sequential administration. Further, the compound of use in the invention may be for administration subsequent to the administration of the one or more other biologically active drug, or the one or more other biologically active drug may be for administration subsequent to the administration of the compound of use in the invention.

The combined preparation may be in the form of a medical kit or package containing the two ingredients in separate but adjacent form. Each ingredient may be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for treating and/or preventing autoimmune and inflammatory disorders, and organ or cell transplant rejection, in a patient, preferably a mammal, more preferably a human being. The method of this invention consists of administering to the patient in need thereof an effective amount of a compound of use in this invention, optionally together with an effective amount of another immunosuppressant or immunomodulator or antineoplastic drug or antiviral agent or phosphodiesterase-4 inhibitor, or a pharmaceutical composition comprising the same, such as disclosed above in extensive detail. The effective amount is usually in the range of about 0.01 mg to 20 mg, preferably about 0.1 mg to 5 mg, per day per kg body weight for humans. Depending upon the pathologic condition to be treated and the patient's condition, the said effective amount may be divided into several sub-units per day or may be administered at more than one day intervals. The patient to be treated may be any warm-blooded animal, preferably a mammal, more preferably a human being, suffering from said pathologic condition. The preferred compounds of use in the present invention are non-sedating. In other words, a dose of such compounds that is twice the minimum dose sufficient to provide analgesia in an animal model for determining pain relief causes only transient (i.e. lasting for no more than half the time that pain relief lasts) or preferably no statistically significant sedation in an animal model assay of sedation (using the method described by Fitzgerald et al. in Toxicology (1988) 49:433-9). Preferably, a dose that is five times the minimum dose sufficient to provide analgesia does not produce statistically significant sedation. More preferably, a compound provided herein does not produce sedation at intravenous doses of less than 10 mg/kg per day or at oral doses of less than 30 mg/kg per day. If desired, compounds provided herein may be evaluated for toxicity (a preferred compound is non-toxic when an immunomodulating amount or a cell anti-proliferative amount is administered to a subject) and/or side effects (a preferred compound produces side effects comparable to placebo when a therapeutically effective amount of the compound is administered to a subject). Toxicity and side effects may be assessed using any standard method. In general, the term "non-toxic" as used herein shall be understood as referring to any substance that, in keeping with established criteria, is susceptible to approval by the United States Federal Drug Administration for administration to mammals, preferably humans. Toxicity may be also evaluated using assays including bacterial reverse mutation assays, such as an Ames test, as well as standard teratogenicity and tumorogenicity assays. Preferably, administration of compounds provided herein within the therapeutic dose ranges disclosed hereinabove does not result in prolongation of heart QT intervals (e.g. as determined by electrocardiography in guinea pigs, minipigs or dogs). When administered daily, such doses also do not cause liver enlargement resulting in an increase of liver to body weight ratio of more than 50% over matched controls in laboratory rodents (e.g. mice or rats). Such doses also preferably do not cause liver enlargement resulting in an increase of liver to body weight ratio of more than 10% over matched untreated controls in dogs or other non-rodent mammals. The preferred compounds of the present invention also do not promote substantial release of liver enzymes from hepatocytes in vivo, i.e. the therapeutic doses do not elevate serum levels of such enzymes by more than 50% over matched untreated controls in vivo in laboratory rodents.

Another embodiment of this invention includes the use of various precursor or "prodrug" forms of the compounds of use in the present invention. It may be desirable to formulate the compounds of use in the present invention in the form of a chemical species which itself is not significantly biologically active, but which when delivered to the body of a human being or higher mammal will undergo a chemical reaction catalyzed by the normal function of the body, inter alia enzymes present in the stomach or in blood serum, said chemical reaction having the effect of releasing a compound as defined herein. The term "prodrug" or "pro-drug" thus relates to these species that are converted in vivo into the active pharmaceutical ingredient. The pro-drugs of use in the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used. For the purposes of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the prodrug has been administered, and without undue toxicity, irritation, or allergic response, and achieving the intended therapeutic outcome.

The present invention will be further described with reference to certain more specific embodiments and examples, but the present invention is not limited thereto. The following examples are given by way of illustration only.

EXAMPLES

Example 1

Analysis of Substrate Binding by a Library of Kinases in the Presence of 5-amino-7-[4-(4-chlorophenoxyacetyl)piperazin-1-yl]-2-(pyridin-3-yl)thiazolo[5,4-d]pyrimidine (Compound of Formula (1))

Kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17× PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

The inhibition of binding of 382 kinases was investigated. Table 1 gives the percentage inhibition of substrate binding of the eight kinases showing the greatest level of substrate binding inhibition in the presence of the compound of formula (1). These 8 kinases were observed to have an $IC_{50}$ binding below 10 μM. The level of inhibition of substrate binding for each of the other 374 kinases by the compound of formula (1) tested in this experiment was less than 50%.

TABLE 1

Inhibition in percentage of binding interaction with 8 different kinases induced by 10 μM of the compound of formula (1).

| kinase | % Inhibition of substrate binding |
| --- | --- |
| LOK | 100 |
| RIOK2 | 94 |
| PI4KIIIβ | 92 |
| YSK4 | 79 |
| ADCK3 | 68 |
| PIK3CB | 56 |
| PAK1 | 54 |
| TESK1 | 51 |

Example 2

Analysis of Kinase Activity Inhibition by the Compound of Formula (1) and 4-[5-amino-2-(pyridin-3-yl)thiazolo[5,4-d]pyrimidin-7-yl]-N-m-tolylpiperazine-1-carboxamide (Compound of Formula (2))

The screening of Example 1 highlighted 8 kinases with an $IC_{50}$ binding below 10 μM. The inhibition activity of compounds of formulae (1) and (2) was screened using commercially available activity assays (LOK, YSK4 and PI3KCB from Millipore; PI4KIIIα, PI4KIIIβ and PAK1 from Invitrogen). The results (shown in Table 2) indicate that the compounds of formulae (1) and (2) are inhibitors of PI4KIIIβ, but not of the other kinases tested.
Materials and Methods
LOK LOK (h) was incubated with 8 mM MOPS pH 7.0, 0.2 mM EDTA, 250 μM KKSRGDYMTMQIG, 10 mM MgAcetate and [γ-$^{33}$P-ATP] (specific activity approx. 500 cpm/pmol, concentration as required). The reaction was initiated by the addition of the MgATP mix. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.
PI3K p110β/p85α (h)

PI3K (p110β/p85α) (h) was incubated in assay buffer containing 10 μM phosphatidylinositol-4,5-bisphosphate and MgATP (concentration as required). The reaction was initiated by the addition of the MgATP mix. After incubation for 30 minutes at room temperature, the reaction was stopped by the addition of stop solution containing EDTA and biotinylated phosphatidylinositol-3,4,5-trisphosphate. Finally, detection buffer was added, which contains europium-labelled anti-GST monoclonal antibody, GST-tagged GRP1 PH domain and streptavidinallophycocyanin. The plate was then read in time-resolved fluorescence mode and the homogenous time-resolved fluorescence (HTRF®) signal determined according to the formula HTRF=10000×(Em665nm/Em620 nm).
YSK4 (h)

YSK4 (h) was incubated with 8 mM MOPS pH 7.0, 0.2 mM EDTA, 250 KKSRGDYMTMQIG, 10 mM MgAcetate and [γ-$^{33}$P-ATP] (specific activity approx. 500 cpm/pmol, concentration as required). The reaction was initiated by the addition of the MgATP mix. After incubation for 40 minutes at room temperature, the reaction was stopped by the addition of 3% phosphoric acid solution. 10 μL of the reaction was then spotted onto a P30 filtermat and washed three times for 5 minutes in 75 mM phosphoric acid and once in methanol prior to drying and scintillation counting.
PI4KA (PI4K alpha)

The 2× PI4KA (PI4K alpha)/PI Lipid Kinase Substrate mixture was prepared in 20 mM Tris, pH 7.5, 0.4% Triton X-100, 5 mM $MgCl_2$, 0.5 mM EGTA. The final 10 μL Kinase Reaction consisted of 75-300 ng PI4KA (PI4K alpha) and 100 μM PI Lipid Kinase Substrate in 7.5 mM HEPES, 10 mM Tris, pH 7.5, 0.2% Triton X-100, 2.5 mM $MgCl_2$, 0.25 mM EGTA. After the 1 hour Kinase Reaction incubation, 5 μL of Detection Mix consisting of a europium labeled anti-ADP antibody, an Alexa Fluor® 647 labeled ADP tracer, and EDTA (to stop the kinase reaction) was added to the assay well. ADP formed by the kinase reaction (in the absence of an inhibitor) displaced the Alexa Fluor® 647 labeled ADP tracer from the antibody, resulting in a decrease in the TR-FRET signal. In the presence of an inhibitor, the amount of ADP formed by the kinase reaction was reduced, and the resulting intact antibody-tracer interaction resulted in a high TR-FRET signal.
PI4KB (PI4K beta)

The 2× PI4KB (PI4K beta)/PI Lipid Kinase Substrate mixture was prepared in 50 mM HEPES pH 7.5, 0.1% CHAPS, 1 mM EGTA, 4 mM $MgCl_2$. The final 10 μL Kinase Reaction consisted of 3.3-42 ng PI4KB (PI4K beta) and 100 μM PI Lipid Kinase Substrate in 32.5 mM HEPES pH 7.5, 0.05% CHAPS, 0.5 mM EGTA, 2 mM $MgCl_2$. After the 1 hour Kinase Reaction incubation, 5 μL of Detection Mix consisting of a europium labeled anti-ADP antibody, an Alexa Fluor® 647 labeled ADP tracer, and EDTA (to stop the kinase reaction) was added to the assay well. ADP formed by the kinase reaction (in the absence of an inhibitor) displaced the Alexa Fluor® 647 labeled ADP tracer from the antibody, resulting in a decrease in the TR-FRET signal. In the presence of an inhibitor, the amount of ADP formed by the kinase reaction was reduced, and the resulting intact antibody-tracer interaction resulted in a high TR-FRET signal.

PAK1

The 2×PAK1/Ser/Thr 19 mixture was prepared in 50 mM HEPES pH 7.5, 0.01% BRIJ-35, 10 mM $MgCl_2$, 1 mM EGTA. The final 10 µL Kinase Reaction consisted of 1.75-30.8 ng PAK1 and 2 µM Ser/Thr 19 in 50 mM HEPES pH 7.5, 0.01% BRIJ-35, 10 mM $MgCl_2$, 1 mM EGTA. After the 1 hour Kinase Reaction incubation, 5 µL of a 1:128 dilution of Development Reagent A was added. After a 60-minute development reaction incubation at room temperature, the fluorescence was read on plate reader and the data analyzed.

TABLE 2

Kinase activity in presence of 10 µM test compound in commercially available selected kinase assays. Results are expressed as percentage of control.

| Kinase | Compound of formula (1) | Compound of formula (2) |
| --- | --- | --- |
| PI3KCB | 100 | 82 |
| LOK | 117 | 98 |
| YSK4 | 108 | 79 |
| PAK1 | 115 | 108 |
| PI4KIIIβ | 1 | 0.5 |
| PI4KA | 99 | 90 |

Example 3

Screening for PI4KIIIβ Inhibitory Activity and Immunosuppressive Activity

The compounds of formulae (1) and (2), as well as 4-[5-amino-2-(pyridin-3-yl)thiazolo[5,4-d]pyrimidin-7-yl]-N-p-tolylpiperazine-1-carboxamide (compound of formula (3)) and 1-{4-[5-amino-2-(pyridin-3-yl)thiazolo[5,4-d]pyrimidin-7-yl]piperazin-1-yl}-2-(4-fluorophenoxy)ethanone (compound of formula (4)) were then investigated to determine their inhibitory effect on PI4KIIIβ activity (inhibition at 10 µM and $IC_{50}$) at Invitrogen according to the protocol described in Example 2 above (Table 3).

Mixed Lymphocyte Reaction (MLR) Assay

The immunosuppressive effect of test compounds was also investigated using MLR assays. Peripheral blood mononuclear cells (PBMCs) were isolated from heparinized blood of healthy donors by density-gradient centrifugation over Lymphoprep. PBMCs were resuspended at a concentration of $1.2×10^6$ cells/mL in complete medium (RPMI-1640 containing 10% heat-inactivated fetal calf serum (FCS) and antibiotics). RPMI1788 cells were treated with 30 µg/mL mitomycin C for 20 min at 37° C., washed four times with medium, and finally suspended in complete RPMI medium to a density of $0.45×10^6$ cells/mL. An amount of 100 µL of each cell suspension was mixed with 20 µL of diluted compound. The mixed cells were cultured at 37° C. for 6 days in 5% $CO_2$. DNA synthesis was assayed by the addition of 1 µCi (methyl-$^3$H)thymidine per well during the last 18 h in culture. Thereafter, the cells were harvested on glass filter paper and the counts per minute (cpm) determined in a liquid scintillation counter.

TABLE 3

PI4KIIIβ $IC_{50}$ (expressed in nM) or inhibition at 10 µM (expressed as % of control).

| Compound | $IC_{50}$ PI4KIIIβ (nM) | % inhibition of PI4KIIIβ @ 10 µM | $IC_{50}$ MLR (nM) |
| --- | --- | --- | --- |
| formula (1) | 9.9 | 99.0 | 30 |
| formula (2) | 14.3 | 99.5 | 2 |
| formula (3) | 5.7 | 98.5 | 3 |
| formula (4) | 21.8 | 95.0 | 25 |

As is clear from the data presented in Table 3, compounds of formulae (1), (2), (3) and (4) all exert significant immunosuppressive activity, with $IC_{50}$ values in the MLR assays of less than 50 nM.

Example 4

Effect of Test Compounds on Cytokine Secretion after α-CD3 Stimulation

The ability of test compounds to inhibit cytokine release by murine splenocytes after stimulation with α-CD3 antibody was also investigated.

$2×10^6$ splenocytes from Balb/C female mice, 8-10 weeks old in 220 µl of complete medium were stimulated with 0.1 µg of hamster anti mouse CD3ε antibody in presence of various concentrations of test compounds. After 24 h of incubation at 37° C., 5% $CO_2$, supernatant were collected and cytokine titers were determined by flow cytometry according manufacturer protocols (MCB United States, Arlington, Mass., USA).

The results are shown in FIG. 1 compared to a DMSO negative control (▼). The compound of formula (1) (●) has $IC_{50}$ values of 76 nM and 204 nM respectively for the inhibition of IL2 (FIG. 1A) and IFNγ (FIG. 1B) release by the splenocytes. The most effective test compound, the compound of formula (3) (■), inhibited IL2 and IFNγ secretion with $IC_{50}$ values of less than 1 nM in each case. Thus, the compound of formula (3) was shown to be as effective at inhibiting IL2 and IFNγ secretion as conventional immunosuppressants such as cyclosporine A (♦). $IC_{50}$ on IFNγ and IL-2 release of Cyclosporine A are 2 nM and less than 1 nM respectively.

Example 5

Collagen-Induced Arthritis Model Assay to Investigate the Immunosuppressive Effect of Test Compounds In Vivo The activity of test compound in an in vivo model, the collagen-induced arthritis model, was investigated. The animals were treated by oral gavage with the compound of formula (3) from the day before the immunization.

DBA1 male mice, 8-10 weeks old, were distributed in 2 groups according to the treatment. Twelve animals received daily treatment with vehicle (1% methylcellulose), twelve others received compound (3) at 40 mg/kg/d in 1% methylcellulose. The treatment initiation started the day before the intradermal injection at the base of the tail of 100 µg of emulsified chicken collagen II in presence of complete Freund adjuvant and added heat-killed *Mycobacterium butyricum*. Daily inspection of the mice was performed to weight animals and quantify disease score according to the following scale (score 0: normal; score 1: redness and/or swelling in one joint; score 2: redness and/or swelling in more than one joint; score 3: redness and/or swelling in the entire paw; score 4: deformity and/or ankylosis). On the day of sacrifice (day 42) serum were collected and anti-collagen II antibody titers were determined by ELISA. Joints were harvested, fixed in 6% paraformaldehyde, decalcified in formic acid 6% for 48 h, sliced and stained by hematoxylin and eosin staining. Hyperplasia of the synovium, infiltration of mono and polymorphonuclear cells and pannus formation parameters were scored blindly. Housing and all experimental animal procedures were approved by the Institutional Animal Care and Research Advisory Committee of the KU Leuven.

Figure 2A:
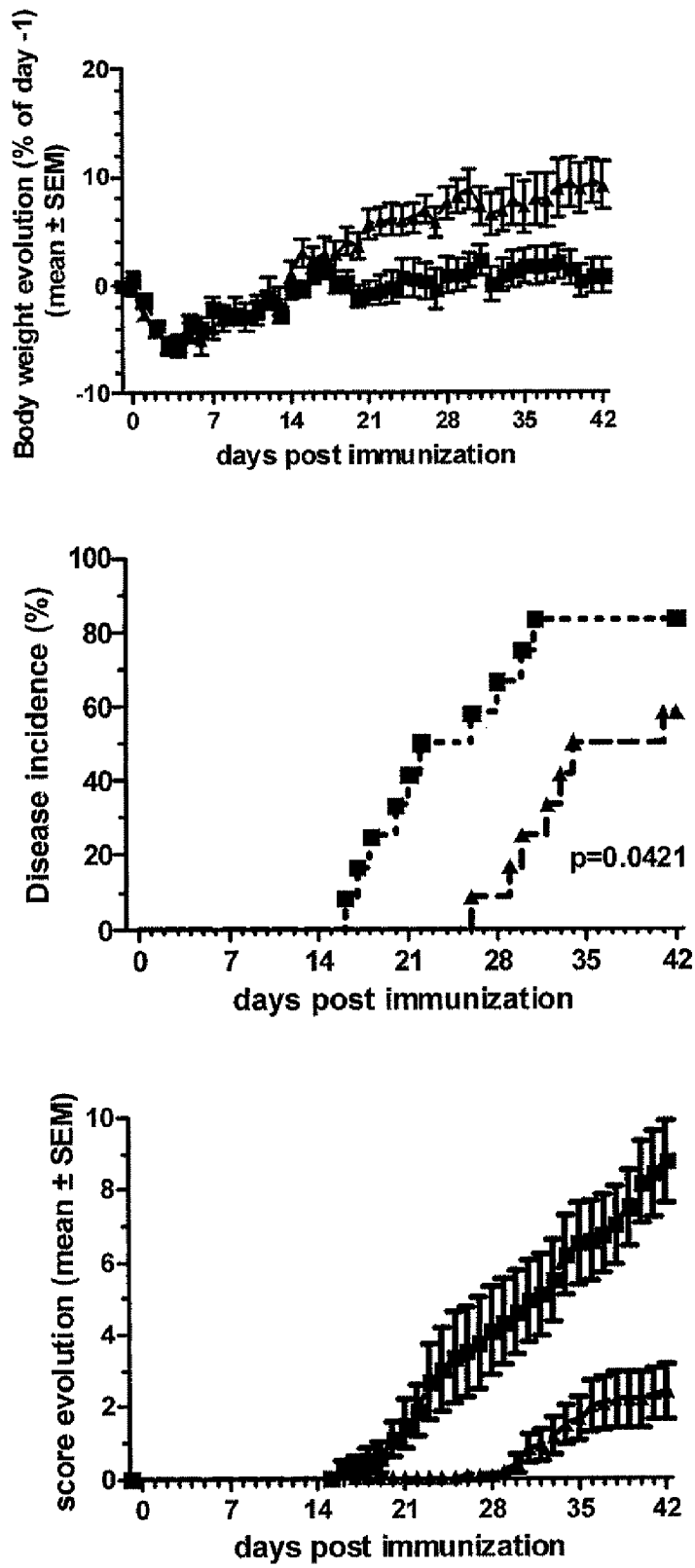
FIG. 2A shows graphs of % weight evolution, % disease incidence and arthritis evolution scores against time for a collagen-induced mouse model of arthritis for vehicle control mice (□) and mice treated with the compound of formula (3) (Δ).
Figure 2B:
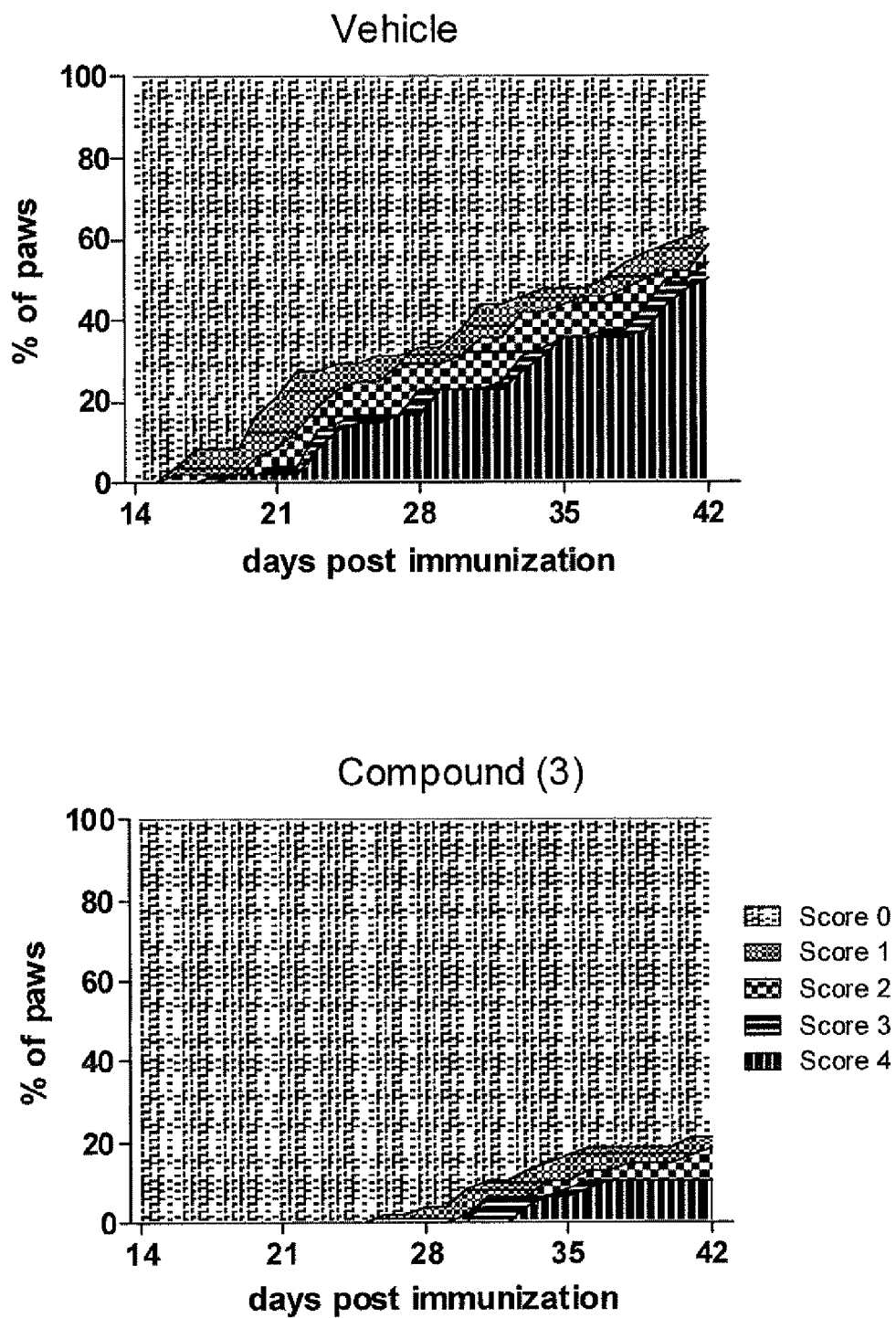
FIG. 2B shows graphs of paw score against time for collagen-induced mouse model of arthritis for vehicle control mice (top graph) and mice treated with the compound of formula (3) (bottom graph).

FIG. 2 illustrates that the compound of formula (3) (▲) (40 mg/kg/d (n=12)) was able to delay the onset of arthritic symptoms and also to decrease symptom severity in a preventive model of arthritis compared to a vehicle control (■) (MC 1% (n=12)).

Figure 3:
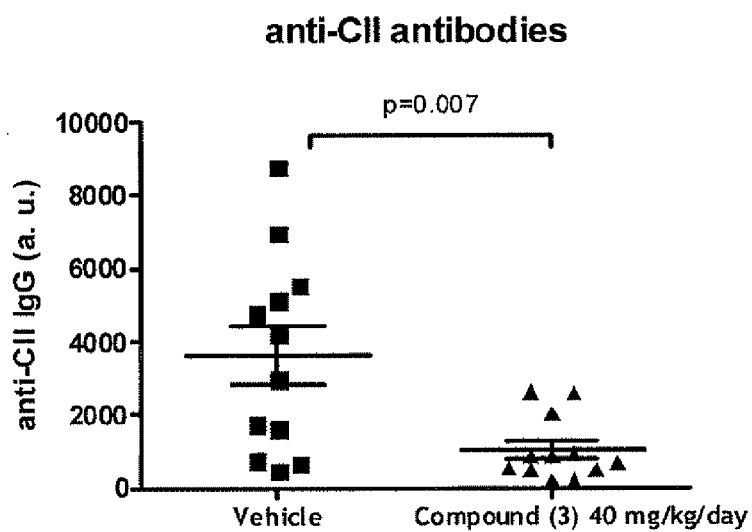
FIG. 3 shows graphs of anti-CII antibody titre (A), hyperplasia scores (B), infiltration scores (C) and pannus scores (D) in the collagen-induced mouse model of arthritis for vehicle control mice and mice treated with the compound of formula (3).
Figure 3:
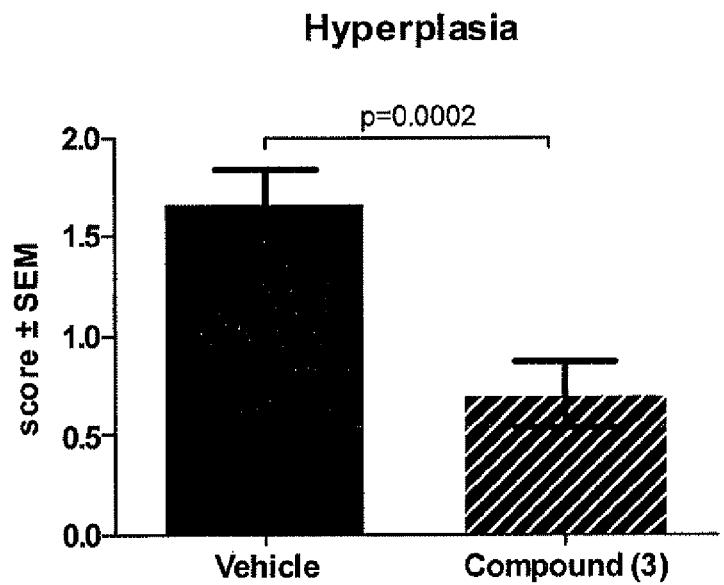
Figure 3:
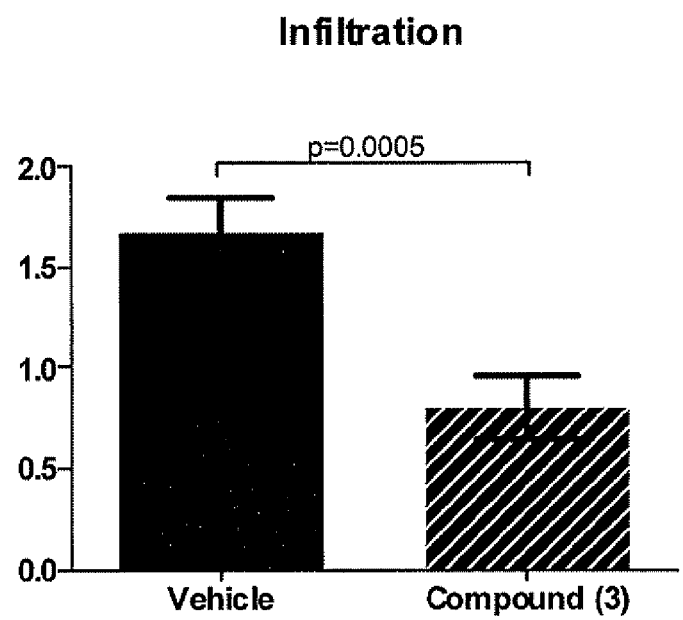
Figure 3:
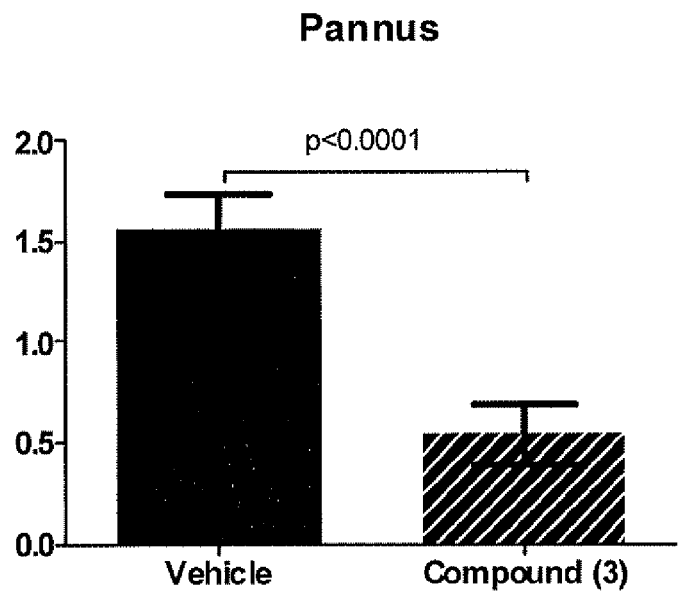

FIG. 3 shows that the compound of formula (3) reduced the anti-CII IgG titre and histological scores in the collagen-induced arthritis mouse model.

Example 6

MLR Assays Using Conventional PI4KIIIβ Inhibitors

T-00127-HEV1 and PIK93 are PI4KHIIIβ inhibitors known in the art. PIK93 has the formula shown below:

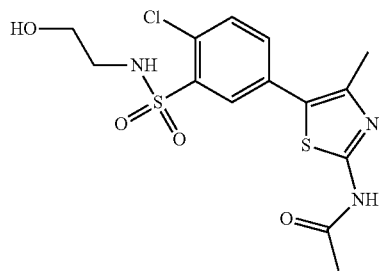 [SMILES: CC(=O)Nc1nc(C)c(-c2ccc(Cl)c(S(=O)(=O)NCCO)c2)s1]

T-00127-HEV1 has the formula:

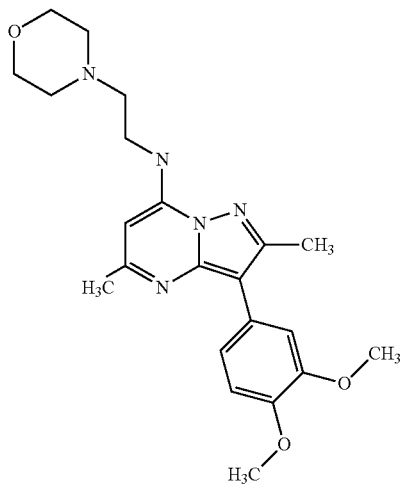 [SMILES: COc1ccc(-c2c(C)nn3c(NCCN4CCOCC4)cc(C)nc23)cc1OC]

T-00127-HEV1 and PIK93 have been shown to have IC50 values of 60 nM and 19nM respectively on PI4KIIIβ activity (Arita M. et al., J Virol. 2011; 85(5):2364-72).

The present inventors have demonstrated for the first time that these PI4KIIIβ inhibitors also possess immunosuppressive activity, as measured using MLR assays. The MLR assays were conducted using the protocol outlined above in Example 3. The results of these MLR assays are shown in Table 4 below.

TABLE 4

IC50 values for T-00127-HEV1 and PIK93 for PI4KIIβ inhibition and MLR assay.

| Test compound | IC$_{50}$ PI4KIIIβ (nM) | IC$_{50}$ MLR (μM) |
|---|---|---|
| T-00127-HEV1 | 60 | 0.842 |
| PIK93 | 19 | 0.401 |

The results disclosed in Table 4 and Table 3 (Example 3) indicate a correlation between PI4KIIIβ inhibition and immunosuppressive activity as measured by MLR.

Example 7

In Vivo Efficacy of the Compound of Formula (1)

Graft Survival

The in vivo efficacy of the compound of formula (1) was studied in a mouse model of cardiac allograft transplantation. Drug vehicle (n=6) or compound of formula (1) (n=4) was given by oral gavage daily, beginning one day prior to transplantation, until day 30 post transplantation. Cyclosporine A (CsA), the major immunosuppressive drug used in organ transplantation, was used as a reference and was also administered by daily gavage (n=4).

Animals treated with vehicle alone rejected their allograft within 6-9 days post transplantation. CsA at the given dose achieved all 4 grafts survival as long as the treatment continued. However, rejection occurred to all 4 grafts within 2 weeks after withdrawal of the treatment. Oral administration of compound (1) (at a dose of 40 mg/kg) resulted in continuous graft survival in 3 out of 4 grafts. The grafts continued beating after withdrawal of the treatment (up to 60 days), indicating the induction of a certain type of graft tolerance. The data are shown in Table 5. These data indicate that compound (1) can suppress a robust in vivo allogeneic response.

TABLE 5

Cardiac graft survival in mice treated with the compound of formula (1).

| Compound | Dose[a] (mg/kg/d) | Surviving days | P value[b] |
|---|---|---|---|
| Vehicle | — | 6, 7, 8, 8, 9, 9 | |
| CsA | 40 | 39, 40, 42, 43 | <0.001 |
| Formula (1) | 40 | 17, >60, >60, >60 | <0.03 |

[a] by daily gavage,
[b] student t test: vs. vehicle

Materials and Methods

Inbreed C57BL/6 H-2b and Balb/c H-2d female mice, 8-10 weeks old, 20-25 g, were used as donor and recipient, respectively. Heterotopic heart transplantation was performed by implanting the donor heart on the neck of recipients using conventional microsurgery techniques. Graft beating was checked daily by inspection and palpation. Cessation of beating indicated graft rejection, which was confirmed by histological examination. Housing and all experimental animal procedures were approved by the Institutional Animal Care and Research Advisory Committee of the KU Leuven.

Animals were randomly divided into 3 groups: (i) Vehicle group: vehicle (30% 2-hydroxypropyl-(3-cyclodextrin) only by daily gavage, n=6; (ii) Reference drug group: CsA 40 mg per kg by daily gavage, n=4; (iii) compound (1) group: 40 mg per kg by daily gavage, n=4. Treatment started one day prior to transplantation (day −1) until day 30 post transplantation.

Example 8

In Vivo Efficacy of the Compound of Formula (3)

The in vivo efficacy of the compound of formula (3) was studied in a mouse model of cardiac allograft transplantation using the materials and methods described in Example 7 above. Animal treated with vehicle rejected the graft within 6-8 days post-transplantation. CsA at 40 mg/kg per day prevented rejection as long as treatment continued in 3 of the 4 grafts. However, all grafts were rejected within 20 days after withdrawal of the treatment on day 30 post-transplantation. Compound (3) at a dose of 20 mg/kg per day slightly prolonged graft survival up to 13 days. Compound (3) at 40 mg/kg per day resulted in continuous graft survival of 4/6 grafts. The grafts (3/4 cases) continuously functioned after stopping the treatment on day 30, suggesting a kind of immune tolerance. The results are shown in Table 6. These results show that the compound of formula (3) effectively suppressed allograft rejection in a dose dependent manner.

TABLE 6

Cardiac graft survival in mice treated with the compound of formula (3).

| Compound | Dose[a] (mg/kg/d) | Surviving days | P value[b] |
|---|---|---|---|
| Vehicle | — | 6, 7, 7, 8 | |
| CsA | 40 | 10, 40, 41, 50 (n = 3) | <0.01 |
| Formula (3) | 20 | 6, 7, 8, 9, 11, 13 | >0.05 |
| Formula (3) | 40 | 9, 11, 50, >60 (n = 3) | <0.01 |

[a]by daily gavage,
[b]student t test: vs. vehicle

Example 9

Graft Survival

The activity of test compound in a mouse model of cardiac allograft transplantation experiment was investigated. The animals were treated by oral gavage with the compound of formula (3) from the day of transplantation until day 30 post transplantation. Animals with beating graft at day 60 were rechallenged with a second graft from the same strain donor or from a third party donor. The results are shown in Table 7.

TABLE 7

Cardiac graft survival and tolerance in mice treated with the compound of formula (3).

| Compound | Dose (mg/kg/d) | Surviving days |
|---|---|---|
| Vehicle | — | 6, 7 |
| Formula (3) | 40 | 12, 14, 16, 42, 43, >60 |
| Formula (3) | 50 | 7, 11, 16, 40, >60, >60 |
| Formula (3) | 60 | 12, 14, 14, 43, 49, >60 |

Animals treated with vehicle alone rejected their allograft within 6-7 days post transplantation. Oral administration of the compound of formula (3) resulted in prolonged graft survival in 3 out of 6 grafts in each group at day 30. Several grafts continued beating after withdrawal of the treatment (up to 60 days), indicating the induction of a certain type of graft tolerance. To evaluate the operational tolerance phenotype, animals with functional graft at day 60 were challenged with a second graft from the same donor strain or from a third party. No treatment was applied. The second grafts from the third party were rejected at day 8 (n=2) whereas second grafts from the same donor strain were functional for more than 90 days (n=2).

Materials and Methods

Inbreed C57BL/6 H-2[b] and Balb/c H-2[d] female mice, 8-10 weeks old, 20-25 g, were used as donor and recipient, respectively. Heterotopic heart transplantation was performed by implanting the donor heart on the neck of recipients using conventional microsurgery techniques. Graft beating was checked daily by inspection and palpation. Cessation of beating indicated graft rejection. The third party donor was C3H H-2[k] female mice, 8-10 weeks old, 20-25 gr. Housing and all experimental animal procedures were approved by the Institutional Animal Care and Research Advisory Committee of the KU Leuven.

Animals were randomly divided into 4 groups: (i) Vehicle group: vehicle (1% HCl; 5% N-methylpyrrolidone; 30% 2-hydroxypropyl-β-cyclodextrin) only by daily gavage, n=2; (ii) compound of formula (3), 40 mg per kg by daily gavage, n=6; (iii) compound of formula (3), 50 mg per kg by daily gavage, n=6; (iv) compound of formula (3), 60 mg per kg by daily gavage. Treatment started the day of transplantation (day 0) until day 30 post transplantation. Animals were dosed at 10, 12.5 or 15 μl/g respectively with a 4 mg/ml solution of compound of formula (3).

The invention claimed is:

1. A method of treating an autoimmune or inflammatory disorder or inhibiting organ or cell transplant rejection that comprises administering to a patient in need of such treatment an effective amount of a compound that inhibits phosphatidylinositol-4-kinase IIIβ (PI4KIIIβ) activity.

2. The method of claim 1 for treating an autoimmune disorder, wherein the autoimmune disorder is selected from a systemic auto-immune disease, an autoimmune endocrine disorder and an organ-specific autoimmune disease.

3. The method of claim 1 for treating an autoimmune disorder, wherein the autoimmune disorder is selected from lupus erythematosus, psoriasis, vasculitis, polymyositis, scleroderma, multiple sclerosis, ankylosing spondylitis, rheumatoid arthritis, Sjogren syndrome, thyroiditis, Addison disease, hemolytic or pernicious anemia, Goodpasture syndrome, Graves disease, idiopathic thrombocytopenic purpura, insulin-dependent diabetes mellitus, juvenile diabetes, uveitis, Crohn's disease, ulcerative colitis, pemphigus, atopic dermatitis, autoimmune hepatitis, primary biliary cirrhosis, autoimmune pneumonitis, autoimmune carditis, myasthenia gravis, glomerulonephritis, asthma, allergy and spontaneous infertility.

4. The method of claim 1 for inhibiting organ or cell transplant rejection, wherein the transplant rejection is selected from the rejection of transplanted or grafted organs or cells, wherein said grafted organs or cells may be either allografts or xenografts.

5. The method of claim 4, wherein the organ transplant rejection is host versus graft reaction disease.

6. The method of claim 4, wherein the organ is selected from kidney, lung, bone marrow, hair, cornea, eye (vitreous), heart, heart valve, liver, pancreas, blood vessel, skin, muscle, bone, intestine or stomach.

7. An assay for identifying a compound for use in treating an autoimmune or inflammatory disorder or inhibiting organ or cell transplant rejection comprising measuring:
- (a) the binding of PI4KIIIβ to a substrate in a sample comprising PI4KIIIβ, the substrate and the compound; and/or
- (b) the activity of PI4KIIIβ in a sample comprising PI4KIIIβ and the compound;

and comparing the binding of PI4KIIIβ to the substrate in (a) or the activity of PI4KIIIβ in (b) to corresponding values from control samples and selecting a compound that inhibits PI4KIIIβ, whereby the selected compound will be useful in treating an autoimmune or inflammatory disorder or inhibiting organ or cell transplant rejection.

8. The assay of claim 7, which further comprises measuring the cell proliferation in a population of peripheral blood mononuclear cells (PBMCs) in a sample comprising the PBMC population and the compound, wherein the PBMCs are subjected to an immunogenic stimulus.

9. The method of claim 1 wherein the compound is selected from
- 5-amino-7-[4-(4-chlorophenoxyacetyl)piperazin-1-yl]-2-(pyridin-3-yl)thiazolo[5,4-d]pyrimidine (formula (1)),
- 4-[5-amino-2-(pyridin-3-yl)thiazolo[5,4-d]pyrimidin-7-yl]-N-m-tolylpiperazine-1-carboxamide (formula (2)),
- 4-[5-amino-2-(pyridin-3-yl)thiazolo[5,4-d]pyrimidin-7-yl]-N-p-tolylpiperazine-1-carboxamide (formula (3)),
- 1-{4-[5-amino-2-(pyridin-3-yl)thiazolo[5,4-d]pyrimidin-7-yl]piperazin-1-yl}-2-(4-fluorophenoxy)ethanone (formula (4)),
- N-(5-(4-chloro-3-(N-(2-hydroxyethyl)sulfamoyl)phenyl)-4-methylthiazol-2-yl)acetamide (PIK93), and
- 3-(3,4-dimethoxyphenyl)-2,5-dimethyl-N-(2-morpholinoethyl)pyrazolo[1,5-a]pyrimidin-7-amine (T-00127-HEV1).

10. The method of claim 6 wherein the compound is 5-amino-7-[4-(4-chlorophenoxyacetyl)piperazin-1-yl]-2-(pyridin-3-yl)thiazolo[5,4-d]pyrimidine (formula (1)).

11. The method of claim 10, wherein the organ is the heart.

12. The method of claim 6 wherein the compound is 4-[5-amino-2-(pyridin-3-yl)thiazolo[5,4-d]pyrimidin-7-yl]-N-p-tolylpiperazine-1-carboxamide (formula (3)).

13. The method of claim 12, wherein the organ is the heart.

* * * * *